United States Patent [19]
Sugarbaker et al.

[11] Patent Number: 5,928,264
[45] Date of Patent: *Jul. 27, 1999

[54] TISSUE GRASPING DEVICE

[75] Inventors: David J. Sugarbaker, Milton; Andy H. Levine, Newton; Nicholas F. Warner, Belmont; Eric E. May, Norfolk, all of Mass.; Lawrence Crainich, Charlestown, N.H.

[73] Assignee: Sugar Surgical Technologies, Inc., Milton, Mass.

[*] Notice: This patent is subject to a terminal disclaimer.

[21] Appl. No.: 08/904,807

[22] Filed: Aug. 1, 1997

Related U.S. Application Data

[63] Continuation-in-part of application No. 08/558,951, Nov. 13, 1995, Pat. No. 5,722,990.
[60] Provisional application No. 60/006,366, Nov. 8, 1995.
[51] Int. Cl.⁶ ..................................... A61B 17/28
[52] U.S. Cl. ............................. 606/207; 606/151
[58] Field of Search ................... 606/1, 10, 113, 606/151, 191, 198, 205–211; 600/201, 204, 206, 210

[56] References Cited

U.S. PATENT DOCUMENTS

| | | |
|---|---|---|
| 848,126 | 3/1907 | Roosevelt . |
| 1,513,367 | 10/1924 | Brix . |
| 2,214,985 | 9/1940 | Bachmann . |
| 4,836,205 | 6/1989 | Barrett . |
| 5,234,443 | 8/1993 | Phan et al. . |
| 5,258,004 | 11/1993 | Bales et al. . |
| 5,312,391 | 5/1994 | Wilk . |
| 5,336,228 | 8/1994 | Cholhan . |
| 5,336,230 | 8/1994 | Leichtling et al. . |
| 5,549,595 | 8/1996 | Freitas ........................................ 606/1 |
| 5,713,897 | 2/1998 | Goble et al. ................................ 606/1 |
| 5,722,990 | 3/1998 | Sugarbaker et al. ....................... 606/1 |

FOREIGN PATENT DOCUMENTS

| | | |
|---|---|---|
| 42 10 724 C1 | 4/1992 | Germany . |
| 42 23 792 C1 | 7/1992 | Germany . |
| 44 18 449 A1 | 5/1994 | Germany . |

*Primary Examiner*—Glenn K. Dawson
*Attorney, Agent, or Firm*—Hamilton, Brook, Smith & Reynolds, P.C.

[57] ABSTRACT

A tissue grasping device is disclosed having a distal end and a proximal end and a central axis extending from end to end. Three tissue engaging tines are located at the distal end, two of which are rotatable, and one of which is spaced from the other two and slidable lengthwise of the plicator. The tines are parallel to one another and to the main axis of the plicator. Actuating mechanism in the form of rack and pinion mechanisms rotate the rotatable tines relative to one another, to grip a portion of the tissue. The non-rotatable times space the portion of the tissue being operated on from the rotatable tine. A push-pull knob mechanism or a thumb-operated lever is employed at the proximal end of the plicator to slide the non-rotatable tine lengthwise of the device to position it in and out of its operating position.

18 Claims, 8 Drawing Sheets

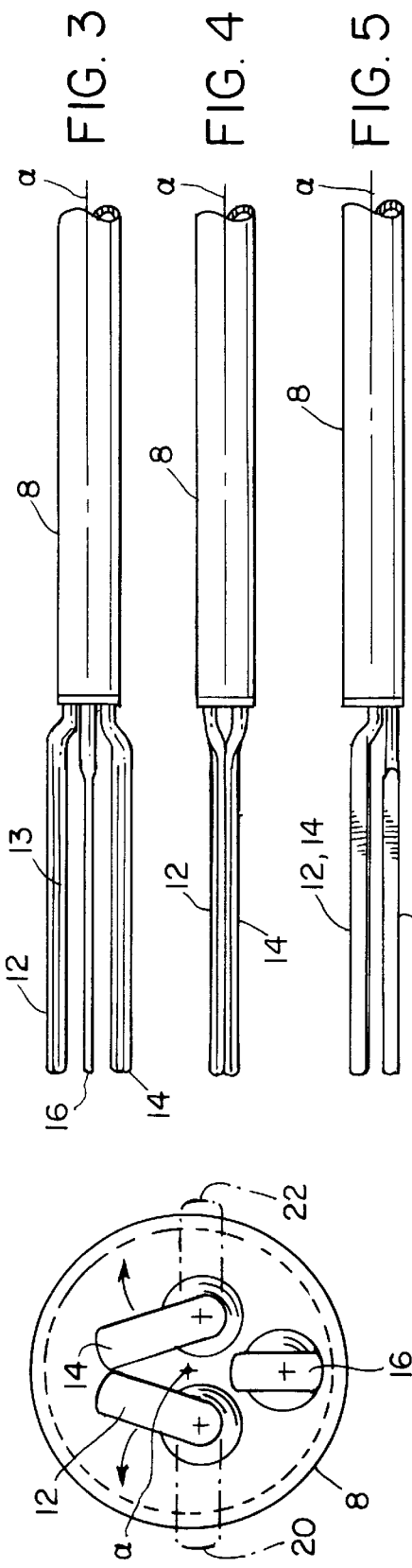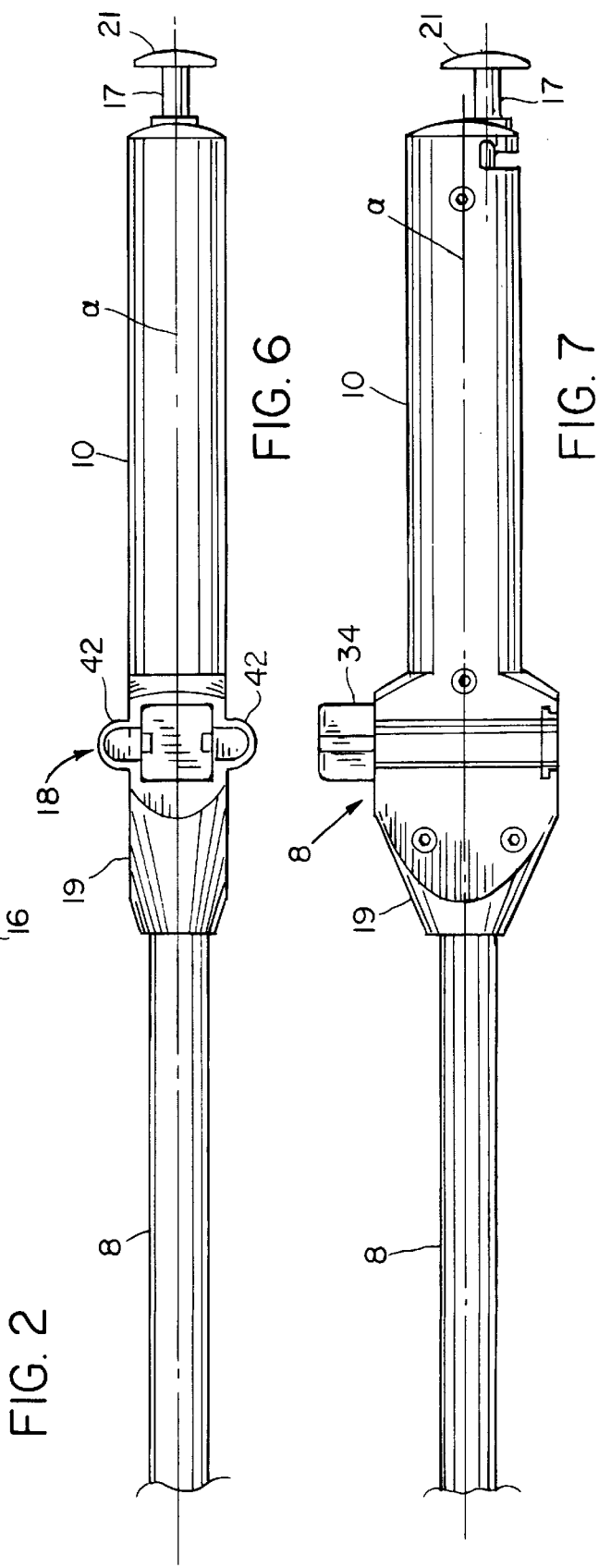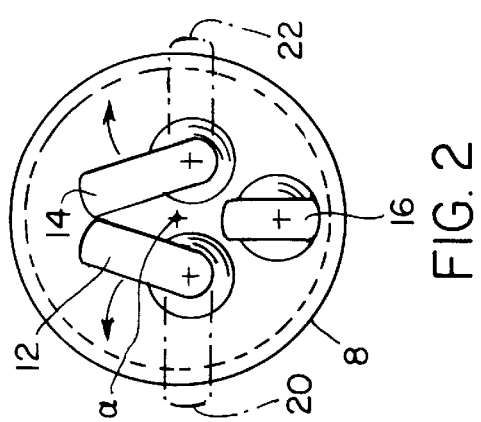

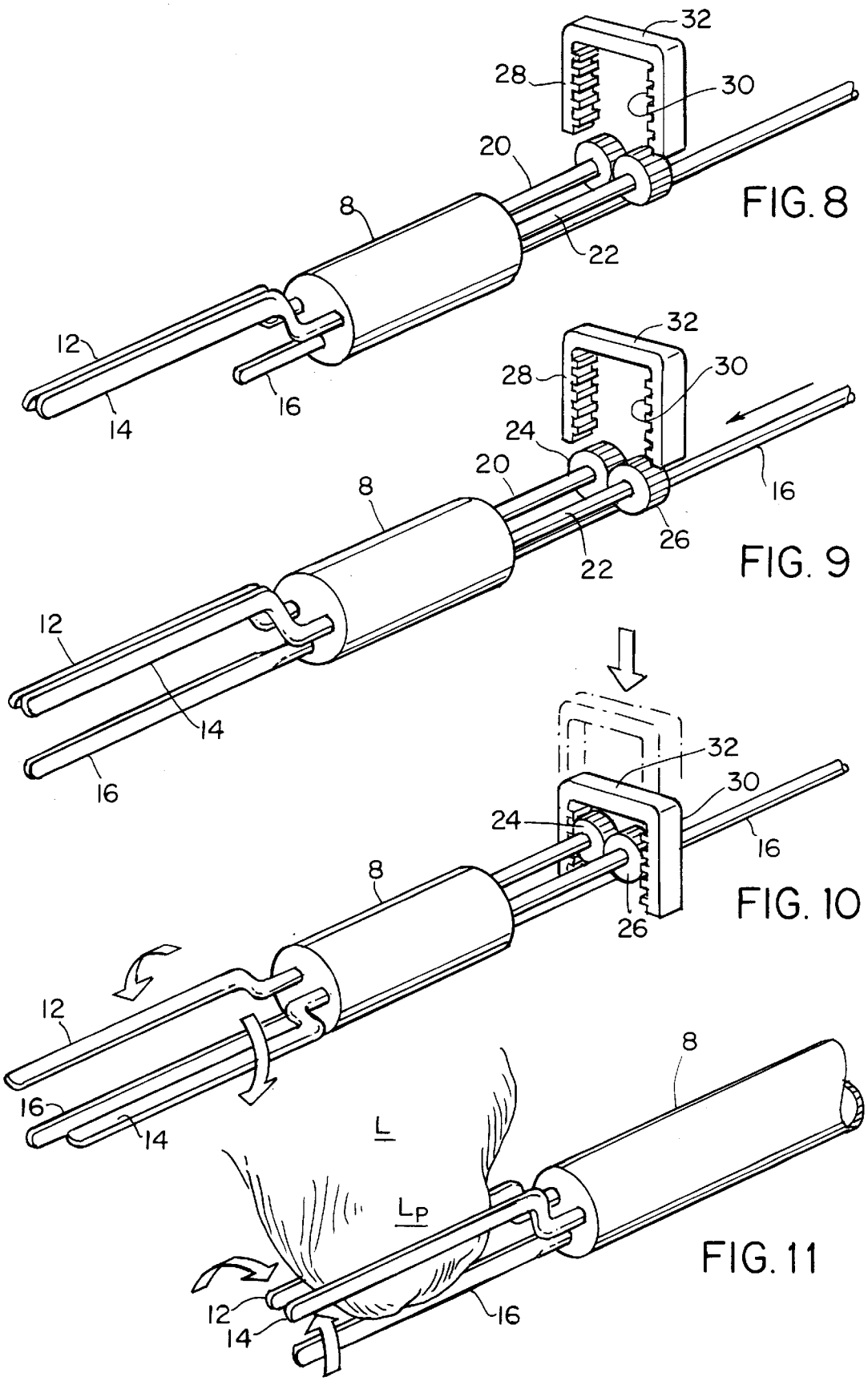

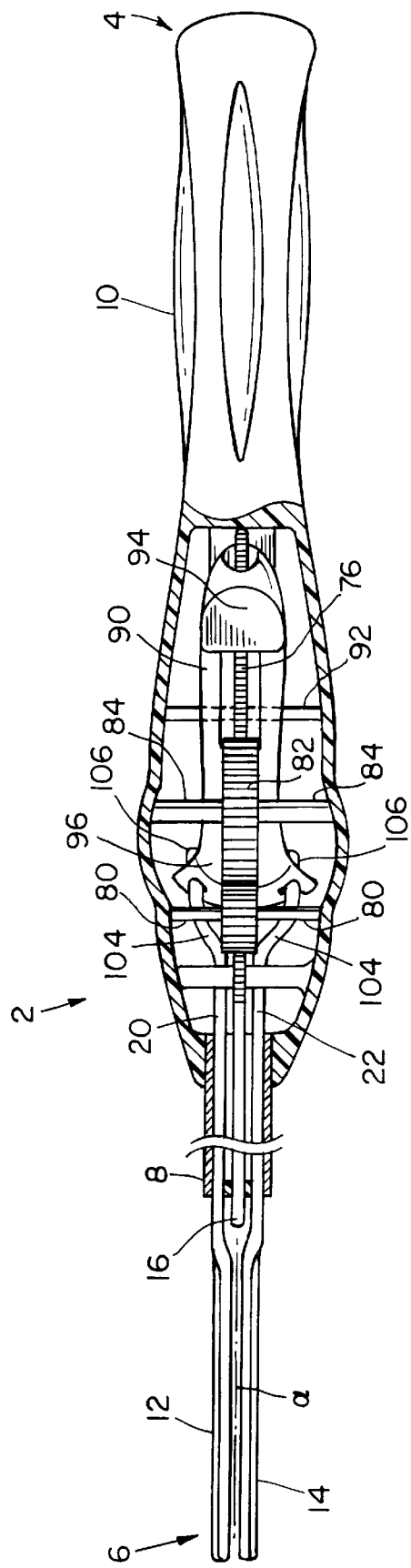

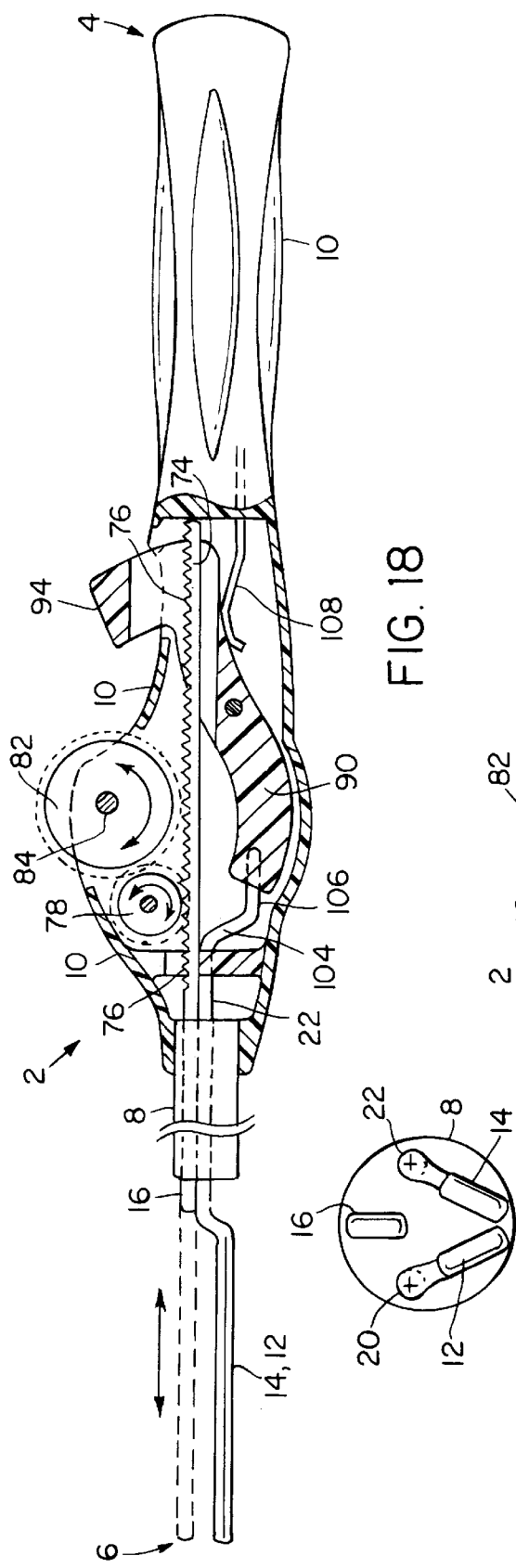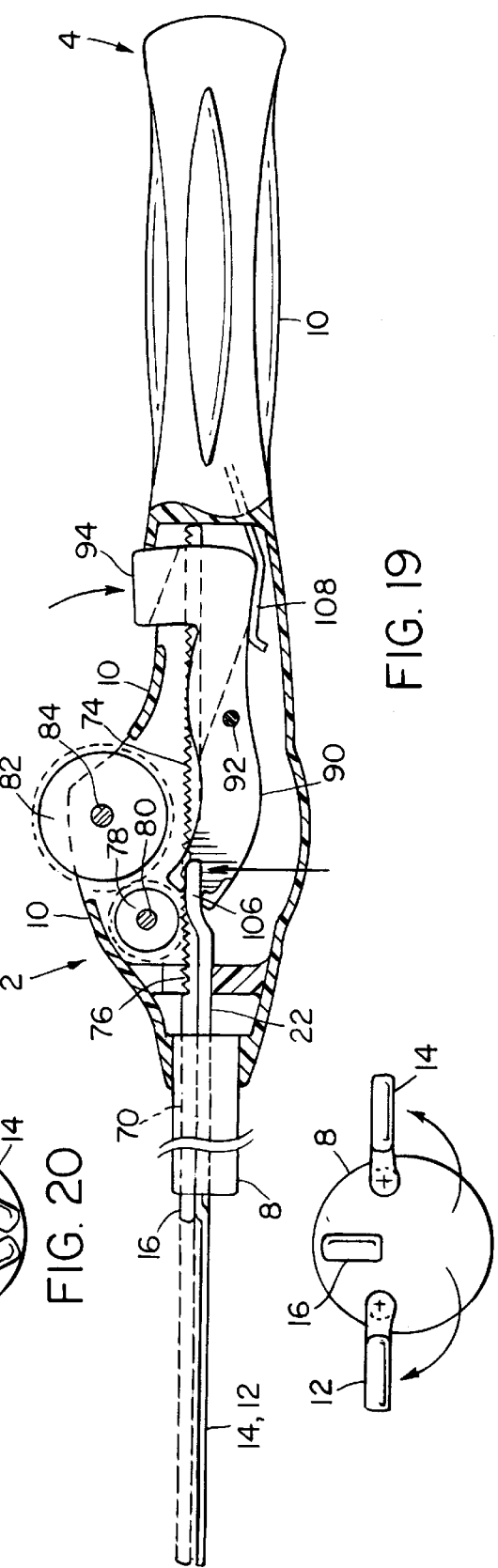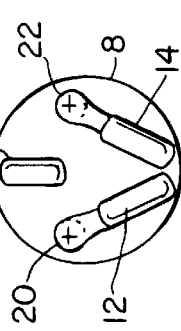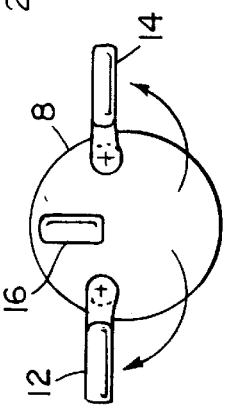

TISSUE GRASPING DEVICE

RELATED APPLICATIONS

This is a continuation-in-part (CIP) application of U.S. application Ser. No. 08/558,951, filed Nov. 13, 1995, now U.S. Pat. No. 5,722,990, which claims priority to Provisional Application No. 60/006,366 filed Nov. 8, 1995, the contents of which are incorporated herein by reference in their entirety.

BACKGROUND OF THE INVENTION

This invention relates in general to tissue manipulating mechanisms useful in surgery and other medical procedures and, more particularly, to a mechanism for grasping tissue atraumatically.

Most medical gripping devices operate much like a pair of scissors or forceps whereby two jaw members move angularly relative to one another about a pivot axis and come together gradually toward the open end. At the pivot end, pinching is positive, while the open end may not come together sufficiently to grasp the desired amount of tissue. In other words, the jaws come together always at an angle. A considerable advantage is to be gained by gripping mechanism where the actual elements which engage the tissue come together in parallelism.

Historically, most medical operations have been performed employing the "open" procedure whereby exterior tissue of the patient is opened and peeled back to expose a relatively large area sometimes including the patient's organs and the like. With this large operative field, the size of surgical instruments is not as important as it is with the newer and more efficient technique of endoscopic surgery. In the endoscopic procedure, one or more small openings are made in the exterior tissue and a small light at the end of a fiber optic is inserted along with a lens also connected by a fiber optic to a video camera. This permits the surgeon to view on a scope what he could not otherwise see. Through one or more additional small openings, the surgeon inserts instruments such as tissue grasping mechanisms, cutting devices and the like which, by their very nature, must be of a small enough diameter to be inserted through the small openings. Some of these instruments are expanded when they are located inside the patient, whereupon the surgeon performs the necessary procedures viewing everything on the scope. The instruments are then withdrawn and only the small incisions have to be closed. Thus, a tissue grasping device which operates with the grasping elements operating in parallel has its value further enhanced if the instrument is collapsible to be able to be inserted through a small aperture and once having been located within the patient at the operative field is expandable to a functional position.

The clamping action of a device which can grasp tissue atraumatically is useful in numerous medical applications. For example, when searching for air leaks in a lung, tissue is placed under water, by flooding the area with saline, and then clamped until bubbles are observed to stop. A clamp of the desired type is easily positioned around the lung for this procedure. A line of staples may then be applied to close off the leaking portion of the lung.

If it is desired to roll a portion of a lung in order to plicate or layer it to receive a line of staples, a composite device having a plurality of parallel tines or gripping elements is desirable. It is advantageous to grasp the lung tissue with opposable, parallel tines and then rotate the device to roll the tissue over the tines.

In another application, when applying staples to lung tissue, it is desirable to remove the air from the tissue as, for example, to collapse it such that a stapler with limited jaw size can be applied.

A grasper having opposable tines is beneficial to this operation by rotating the instrument to squeeze the air out of the lung.

Emphysematous blebs can cause at least two problems. One is pneumothoraces as the bleb leaks and the other is obtrusive disease as the bleb or emphysematous tissue overfill the chest. Frequently, both of these diseases are treated by resuction of the diseased lung or by plication. In the plication technique, the lung tissue is rolled and a non-cutting stapler is placed over the layers of lung held by a clamp. A stapler is positioned over the plicated tissue and the grasping mechanism is withdrawn. The stapler is then fired and the tissue remains in place but the bleb has been sealed or the volume of the lung has been reduced without removing any tissue.

One of the largest causes of death in the United States at the present time is attributed to the final stages of emphysema. It is generally believed that lung volume reduction surgery can be of substantial benefit in addressing the physiologic problem (air flow limitation).

Lung volume reduction surgery alone is not the answer. Rehabilitation or conditioning programs are limited by air flow reduction to the lungs. The surgery is intended to improve air flow by changing the mechanical relationship between the lung, chest, wall and diaphragm which does result in improved exercise tolerance. Consequently, lung reduction surgery is most beneficial to patients who are participating in rehabilitation. It is particularly beneficial to patients with hyperexpanded lungs and chest wall associated with air flow obstruction.

While the present invention contemplates a device having general surgical applications, it will be illustrated in lung plication. One of the ways to reduce or eliminate the effects of emphysema is to reduce the size of the diseased lung. This can be done by stapling it, i.e., folding it and then securing it in its folded position. A reduction in volume of 30% has been found to be beneficial, particularly when accompanied by a reconditioning program. The present invention is directed to a device for reducing the size of the lung by grasping it with an atraumatic device, rolling a portion of the lung upon itself and exposing the portion to be stapled.

SUMMARY OF THE INVENTION

The grasping device is a hand-held surgical tool having a distal end and a proximal end and an axis extending from end to end. Lung engaging tines are located at the distal end. Two of the tines are rotatable relative to each other about axes parallel to the central axis of the device and to the third tine which is not rotatable but is constructed to slide axially of the device also parallel to the main axis.

The rotating tines are spaced from each other and from the non-rotatable tine. They are mounted at the ends of rotatable rods in offset relationship such that rotation of each rod induces its respective tine to pivot initially away from each other and then are returnable to their original positions by spring force in substantial engagement with each. Each tine rod mounts a pinion at its proximal end which pinion is engagable with a separate rack. The racks are joined together in a U-shaped frame such that when pressure is applied to the frame against spring pressure, both tines are rotated away from each other in parallelism into an open position. Subsequent reduction of pressure on the frame allows springs to return the tines to their original position.

The third tine is non-rotatable but is mounted on a rod which slides lengthwise of the device and may be moved manually into and out of an operative position in close proximity to the rotatable tines by a push-pull mechanism.

It is also within the scope of this invention that the slidable tine can be actuated by a rack and pinion mechanism. In this embodiment, the rod which mounts the non-rotatable tine has a toothed rack which is engaged by a pinion gear mounted for rotation in the device. The pinion gear is engaged by a finger (or thumb) operated gear also mounted for rotation in the grasping device.

The above and other features of the invention including various and novel details of construction and combination of parts will now be more particularly described with reference to the accompanying drawings and pointed out in the claims. It will be understood that the particular tissue grasping device embodying the invention is shown by way of illustration only and not as a limitation of the invention. The principles and features of this invention may be employed in varied and numerous embodiments without departing from the scope of the invention.

BRIEF DESCRIPTION OF THE DRAWINGS

FIG. 2 is a view on enlarged scale of the end of the device of FIG. 1 viewed from the distal end.

FIG. 3 is a top view of the distal end with tines in open position.

FIG. 4 is a top view of the distal end with the tines in closed position.

FIG. 5 is a side view of the distal end.

FIG. 6 is a top view of the proximal end.

FIG. 7 is a side view of the proximal end.

FIGS. 8 through 14 are a series of schematic views of the device in the process of plicating a lung rendered seriatim.

FIG. 17 is a top perspective view with parts broken away for clarity of the embodiment shown in FIG. 15.

FIG. 18 is a side view partially in section of the FIG. 15 embodiment.

FIG. 19 is another side view partially in section of the FIG. 15 embodiment.

FIG. 20 is a front view of the removable tines in closed position, resulting from the actuating mechanism for moving the tines being in the FIG. 18 position.

FIG. 21 is a front view of the movable tines in the open position, resulting from the actuating mechanism being in the FIG. 19 position.

DETAILED DESCRIPTION OF THE INVENTION

Figure 1:
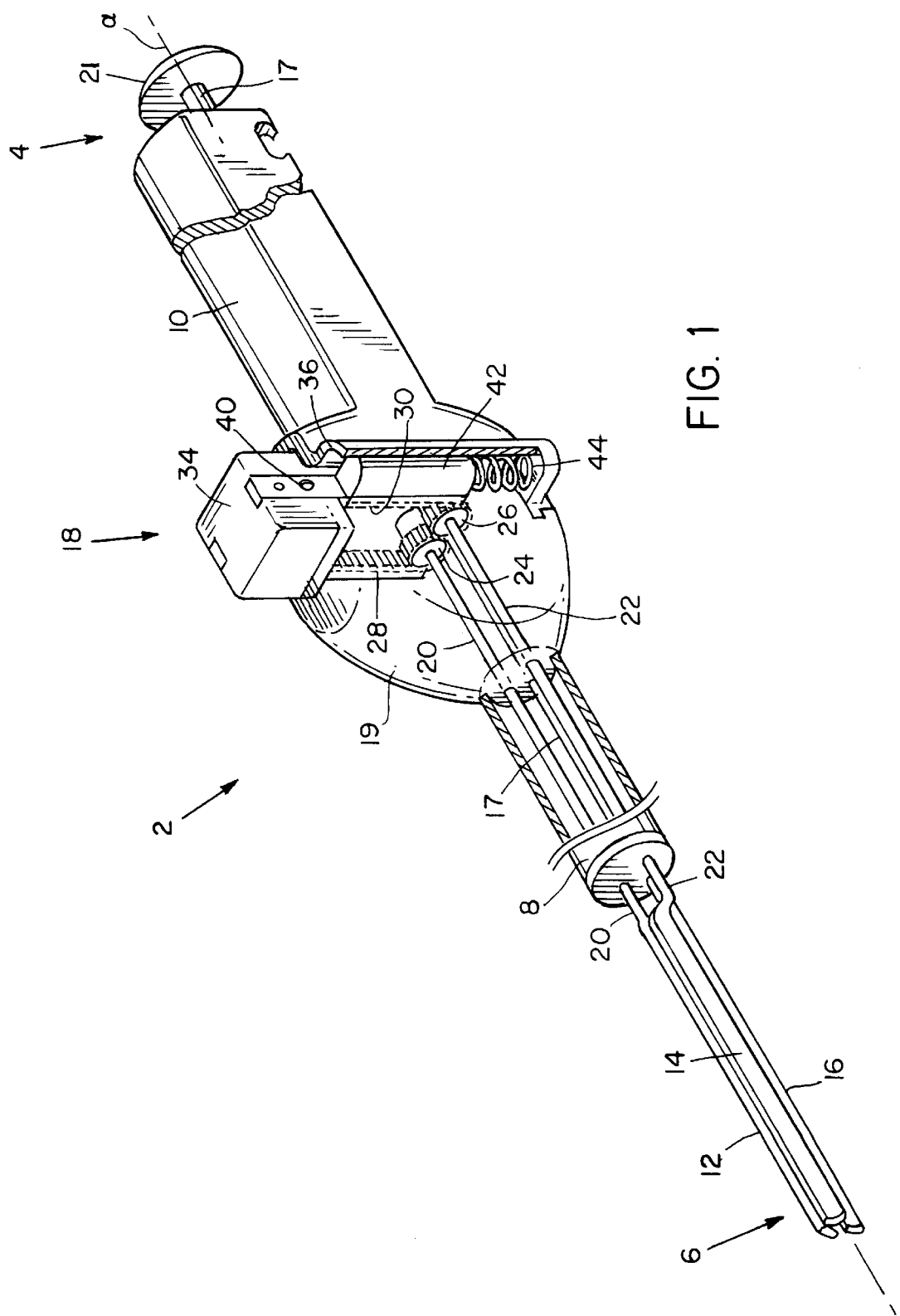
FIG. 1 is a perspective view partially broken away and partially in section of an atraumatic tissue grasping device embodying the principles of the present invention.

While the invention may be embodied in many devices, it will be described in detail with reference to a lung plicator which will be seen in FIG. 1 in perspective. The device, generally indicated 2, has a proximal end 4, a distal end 6 and a central axis α. Near the distal end is a circular barrel 8 (shown foreshortened and partially broken away in FIG. 1) and near the proximal end is a handle 10. A pair of parallel rotatable tines 12 and 14 extend from the barrel 8 at the distal end. A non-rotatable, but slidable, tine 16 also extends from the barrel 8 at the distal end 6. It is parallel to the axis α and the tines 12 and 14 and is connected to a rod 17. Operating mechanism for rotating the tines 12 and 14 is generally indicated 18, and in located in a housing 19. The housing is positioned between the handle 10 and the barrel 8. An actuator knob 20 projecting from the rod 17 at the proximal end is employed for sliding the non-rotatable tine 16 manually back and forth lengthwise of the device.

The rotatable tines 12 and 14 are parallel to each other and both parallel to the axis α. They are respectively offset from operating rods 20 and 22 which extend through the barrel and from there to the operating mechanism 18. The operating rods 20 and 22 mount pinions 24 and 26, respectively. The pinions 24 and 26 engage racks 28 and 30 projecting downwardly forming the legs of a substantially U-shaped bracket or actuator having a bridge 32, better seen in FIGS. 8, 9 and 10. An block 34 is mounted on top of the bridge 32 and projects from the housing 19. The block moves vertically in the housing 19. Guiding the block 34 for movement in the direction transversely of the central axis α of the device, are guideways 36 located in the housing 19. Only one guideway is seen in FIG. 1. Screws 40 secure arcuate guides 42 (only one of which is seen in FIG. 1) to block 34 for slidable movement in the guideways 36. The guides 42 are urged upwardly by compression springs 44 fitting within the guideways 36.

Manually depressing the block 34 causes the racks 28 and 30 to move downwardly against the force of the compression springs 44. The rods rotate the pinions 24, 26 in opposite directions. This motion, in turn, rotates the rods 20 and 22, thus causing the tines 12 and 14 to rotate in parallelism about the axis of its own operating rod 20, 22, respectively and outwardly relative to the axis α of the plicator (see FIG. 2).

Releasing pressure on the block 34 permits the compression springs 44 to rotate the pinions 24, 26 in the opposite direction causing the tines 12 and 14 to return to their original or closed position.

The plicating device is operated in the following manner. The patient is prepared for surgery in routine fashion. It may be open surgery or endoscopic surgery. If the surgery is endoscopic, an incision is made in the chest wall and a fiber optic light and camera lens is inserted. The light illuminates the operative field and the lens captures an image of the interior of the chest cavity which is displayed on a television monitor. A second opening is formed in the chest cavity for the insertion of the device and a third incision is made for the insertion of a linear stapler. Guiding mechanism such as described in U.S. Pat. No. 5,279,573 to Sugarbaker may be employed to maintain the incisions in open condition and to align and clamp the fiber optic cable in the desired position. Similar mechanics may be used to receive the plicating device as well as the stapler.

If open surgery is performed, the fiber optic light the camera lens and the guiding mechanism are not used. The distal end 6 of the stapler is first inserted with the tines 12 and 14 in their closed parallel positions as shown in FIGS. 2 and 4. The tine 16 may either be in the advanced position or retracted. If it has been inserted in retracted position, the next step is seen in FIG. 9 whereupon the knob 20 is urged forward to extend the tine 16 out of the housing and into spaced parallel relationship to the tines 12 and 14. Thereafter, the block 34 is pressed downwardly by the surgeon to rotate the tines 12 and 14 to their open positions as seen in FIG. 10.

The plicator is next advanced toward the lung L seen in FIG. 11 passing on either side of a portion of the lung designated $L_p$. The block 34 is then released allowing the springs 44 to rotate tines 12 and 14 toward one another. The patient's $L_p$ lung is thereby firmly gripped between the rotatable tines.

Figure 12:
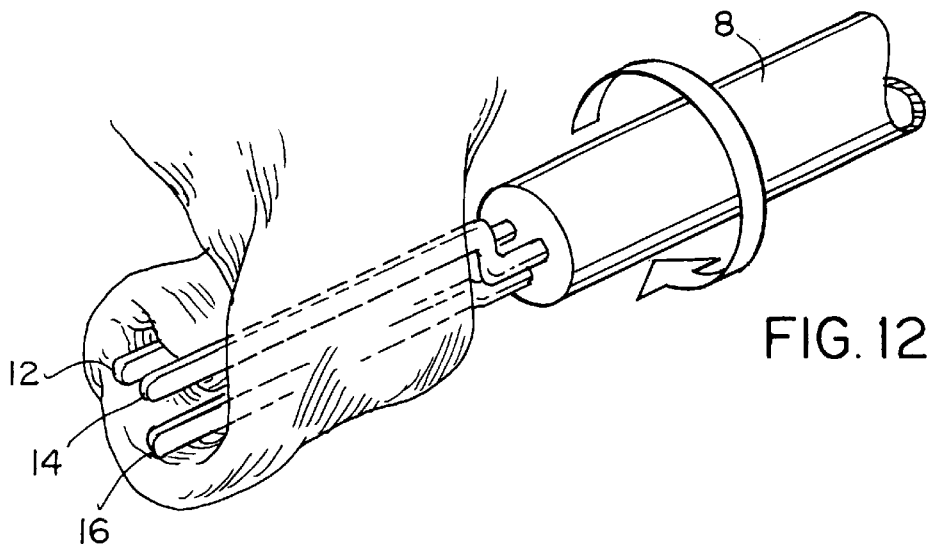
Figure 13:
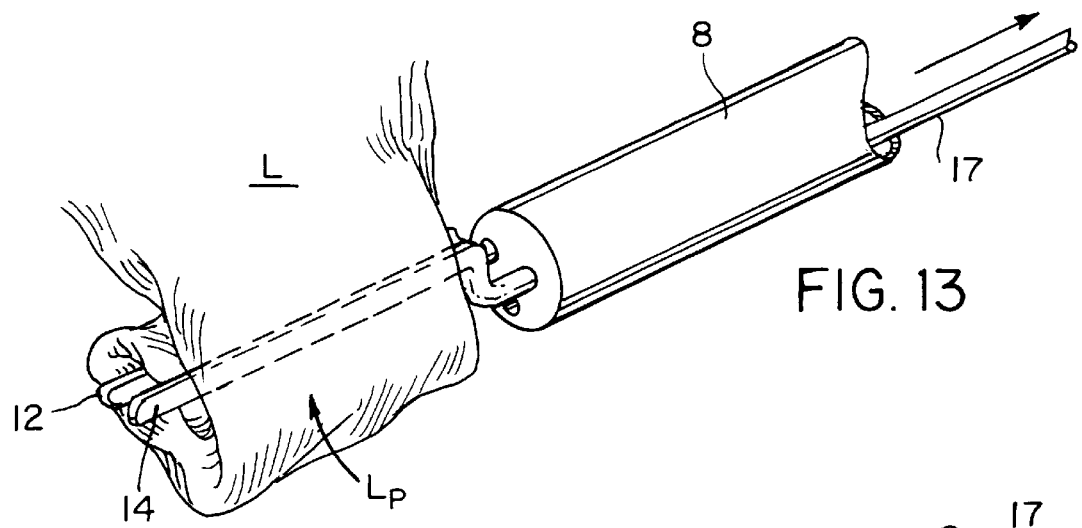

Next referring to FIG. 12, the entire tissue grasping mechanism is rotated in the direction of the arrow in FIG. 12 to roll the lung first around the tine 12, subsequently around the non-rotatable tine 16, and then into contact with the time 14. After rolling is complete, tine 16 may be withdrawn from its operative position by pulling on the knob 20 leaving the lung gripped between the tines 12 and 14 with a projection $L_p$ in position to be stapled. Alternatively, the tine 16 may remain in place.

Figure 14:
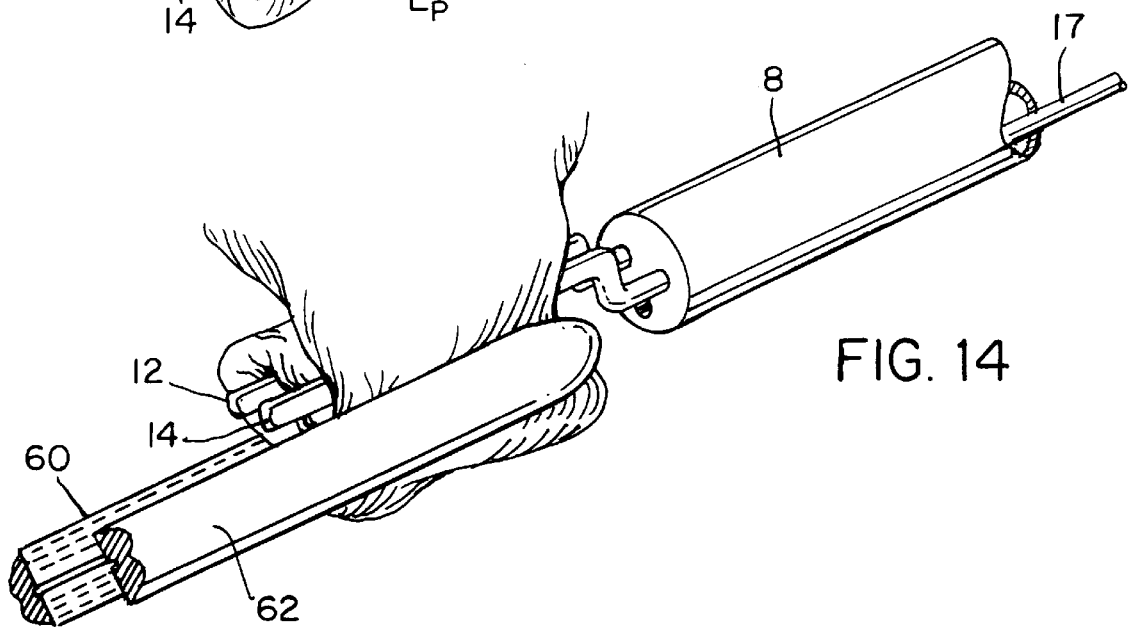

The next step is to advance the stapler, shown only partially in FIG. 14, as having an anvil portion 60 and a driver 62. The stapler may be positioned as shown in FIG. 14 with the tine 16 withdrawn. Similarly, it may be inserted between the tines or even above the tines if the surgeon so desires. The tissue grasping device may be completely withdrawn after the stapler is in place since the tissue is then held by the stapler. The stapler is then fired, inserting parallel lines of staples in the lung portion $L_p$ while it is in the plicated position. The stapler is next opened and withdrawn from the patient.

Figure 15:
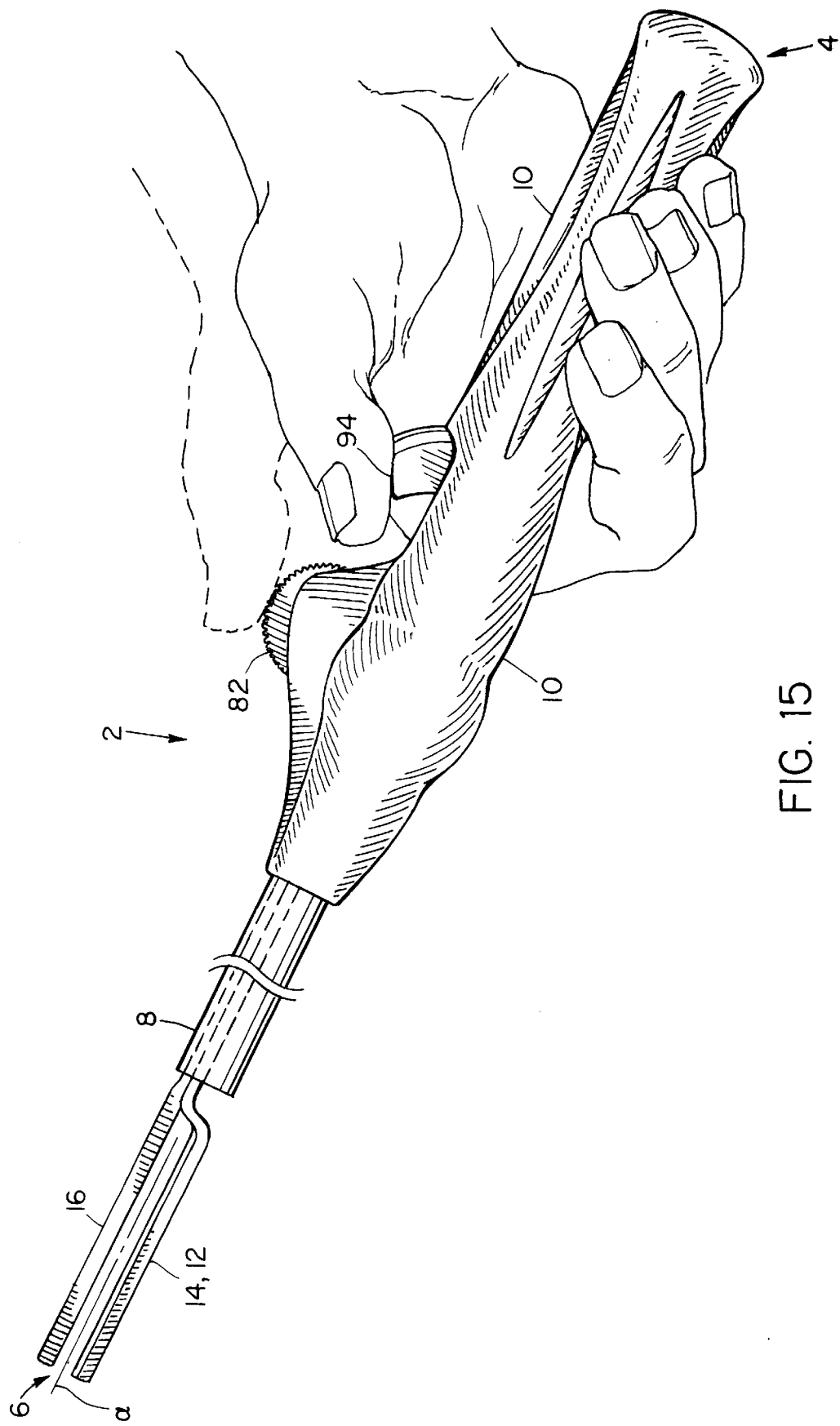
FIG. 15 is a perspective view of another embodiment of the atraumatic tissue grasping device of FIG. 1.

Another embodiment of the invention will be seen in FIG. 15 et sec. As in the FIG. 1 embodiment, the lung plicator 2 has a proximal end 4, a distal end 6, a central axis α, a circular barrel 8 and a handle or hand grip 10 at the proximal end 4. There are parallel rotatable tines 12 and 14 at the distal end and a non-rotatable slidable tine 16 also at the distal end. As thus far described, the elements are the same as in the FIG. 1 embodiment.

Figure 16:
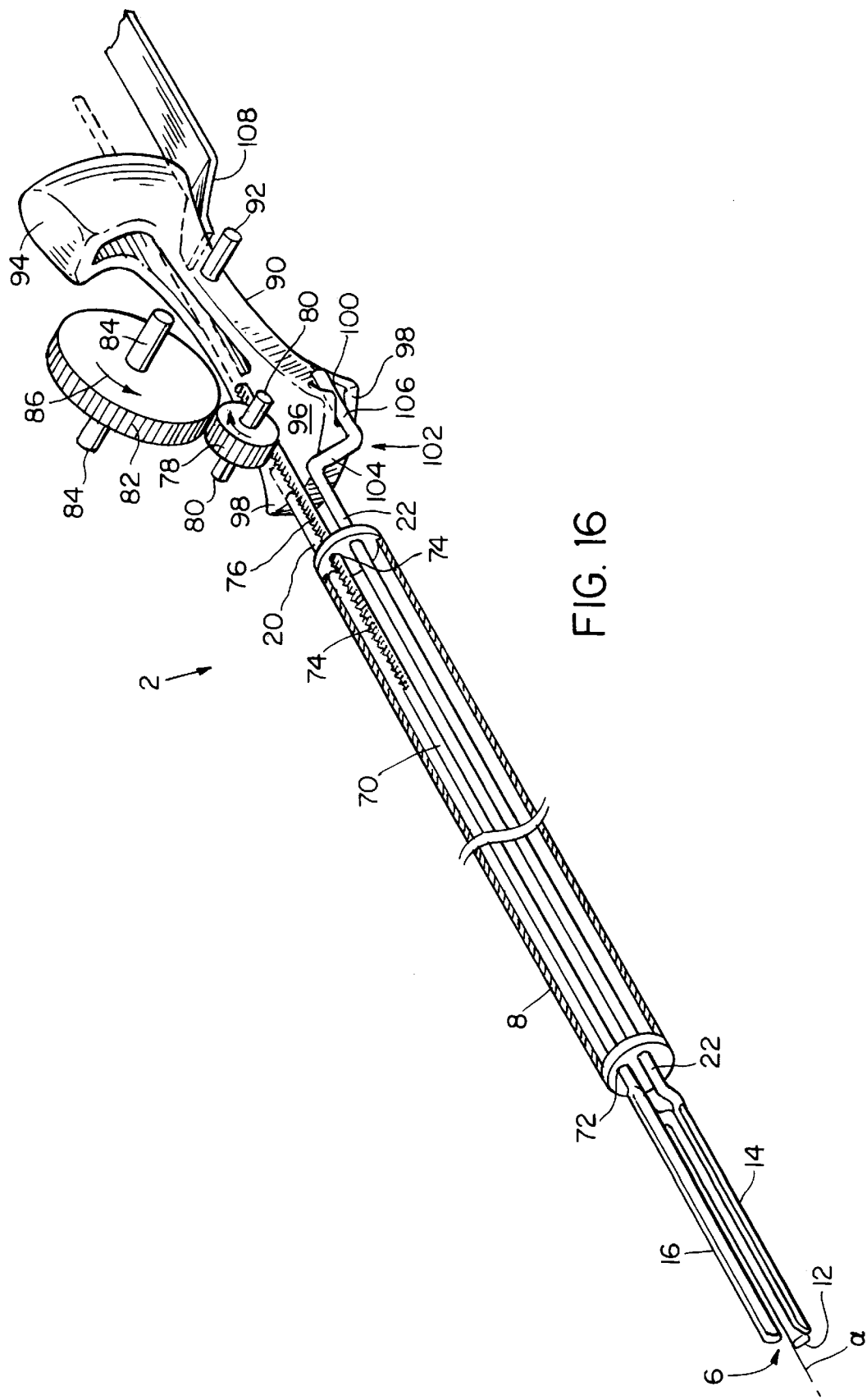
FIG. 16 is a perspective view with parts broken away for clarity of the embodiment shown in FIG. 15.

Referring next to FIGS. 16 to 19, mechanism for advancing and retracting the non-rotatable slidable tine 16 will be described. A rod 70 is a linear extension of the tine 16 and is guided for movement in the barrel 8 in guideways 72 and 74 (FIG. 16). The proximal end of the rod 70 has a rack 74 with a linear array of teeth 76. The teeth are engagable with a pinion gear 78 which is mounted for rotation in the handle 10 on stubby shafts 80. The pinion 78 is engaged by a finger operated driving gear 82 also mounted for rotation in the handle 10 on stubby shafts 84. As will be seen in FIG. 16, rotation of the driving gear 82 in the direction of the arrow 86 in FIG. 16 causes the pinion gear 78 to rotate in the opposite direction, thus moving the toothed rack, the rod 70 and, thus, the non-rotatable tine out of the guideway 72 in the barrel 8 in the distal direction. Opposite rotation of the driving gear 82 withdraws the non-rotatable tine 16 back toward and into the housing 8.

The extending mechanism thus described for moving the non-rotatable tine 16 toward and away from the distal end 6 parallel to the axis α and the rotatable tines 12 and 14 is the equivalent of the push-pull mechanism including the rod 17 and the actuator knob 21 of the FIG. 1 embodiment.

Another embodiment shown in FIGS. 15–21 is the mechanism for rotating the tines 12 and 14 in arcs. As in the FIG. 1 embodiment, movable tine 12 is secured in offset relationship to an operating rod 20 and the movable tine 14 is connected also in offset relationship to an operating rod 22.

A thumb actuated lever 90 is pivoted on a pin 92 in the handle portion 10 of the device or tool 2. One end of the lever 90 has a thumb rest 94 and the opposite end 96 is generally fan-shaped and has outwardly extending noses 98, each of which is provided with a slot 100. The operating rod 22 is provided with an offset crank 102 as is the rod 22. The cranks 102 (one of which is best seen in FIG. 16) includes a segment 104 extending outwardly from the rod 22 and a terminal portion 106 which extends parallel to the rod 22. Portions 106 are received within the slots 100 in the noses 98 of the thumb lever 90.

In the rest position, the lever occupies the position shown in FIG. 18 with the thumb portion 94 of the lever 90 being elevated by a leaf spring 108 fixed in the handle 110 and engagable with the bottom of the lever 90. In the rest position, the tangs 12 and 14 occupy the position shown in FIG. 20, that is, the closed position. To open the tangs, the surgeon presses on the finger portion 94 of the lever 90 against the force of the spring 108 and, through the linkage 102 and the rods 22, moves the tines 12 and 14 to the FIG. 21 position. Release of the lever permits the spring 108 to return the lever 92 to the FIG. 18 position.

The FIG. 15 embodiment of the device is operated to perform the same functions that were described with reference to the FIG. 1 embodiment.

The invention claimed is:

1. A surgical device comprising:

a tissue manipulating mechanism having a proximal end and a distal end;

at least two rotatable, parallel, tissue engaging tines extending from the distal end of the mechanism and movable in arcs toward and away from each other in parallelism;

a non-rotatable tine extendable from the distal end in a linear path parallel to the movable tines;

extending mechanism connected to the non-rotatable tine for moving said non-rotatable tine toward and away from the distal end parallel with the rotatable tines; and actuating mechanism connected to the movable tines for moving said movable tines in arcs.

2. A surgical device according to claim 1, wherein the actuating mechanism comprises manually operated rack and pinion gears.

3. A surgical device according to claim 2, wherein the actuating mechanism is a finger operated lever pivotally mounted at the proximal end and engagable with the rack and pinion gears.

4. A surgical device according to claim 1, wherein the extending mechanism is a manually operated push-pull device.

5. A surgical device according to claim 1, wherein the extending mechanism is a finger operated gear and pinion engagable with a rack on the non-rotatable tine.

6. A surgical device comprising:

a tissue manipulating mechanism having a central axis, a proximal end and a distal end;

at least one, rotatable, tissue engaging tine extending from the distal end and movable in an arc in parallelism with the axis;

a non-rotatable tine movable linearly from the proximal end toward and away from the distal end in parallelism with the axis;

actuating mechanism connected to the at least one rotatable tine for rotating said one rotatable tine in an arc toward and away from the non-rotatable tine for releasably gripping and manipulating tissue.

7. A surgical device according to claim 6, wherein the actuating mechanism comprises manually operated rack and pinion gears.

8. A surgical device according to claim 6, wherein the actuating mechanism is a finger operated lever pivotally mounted at the proximal end and engagable with the rack and pinion gears.

9. A surgical device comprising:

a tissue manipulating mechanism having a central axis, a proximal end and a distal end;

at least two rotatable, tissue engaging tines extending from the distal end and movable in arcs in parallelism with the axis and with each other;

a non-rotatable tine movable linearly from the proximal end toward and away from the distal end in parallelism with the axis;

extending mechanism connected to the non-rotatable tine for moving said non-rotatable tine toward and away from the distal end parallel with the rotatable tines; and actuating mechanism for rotating said rotatable tines in arcs toward and away from the non-rotatable tine for releasably gripping and manipulating tissue.

10. A surgical device according to claim 9, wherein the actuating mechanism comprises manually operated rack and pinion gears.

11. A surgical device according to claim 10, wherein the actuating mechanism is a finger operated lever pivotally mounted at the proximal end and engagable with the rack and pinion gears.

12. A surgical device according to claim 9, wherein the extending mechanism is a manually operated push-pull device.

13. A surgical device according to claim 9, wherein the extending mechanism is a finger operated gear and pinion engagable with a rack on the non-rotatable tine.

14. A surgical device comprising:

a tissue manipulating mechanism having a proximal end and a distal end;

at least two rotatable, parallel, tissue engaging tines extending from the proximal end of the mechanism and movable in arcs toward and away from each other in parallelism;

a non-rotatable tine extendable from the distal end in a linear path parallel to the movable tines;

extending mechanism for moving the non-rotatable tine toward and away from the distal end parallel with the rotatable tines;

actuating mechanism for moving the movable tines in arcs; and a hand grip at the proximal end of the device mounting the extending mechanism and the actuating mechanism.

15. A surgical device according to claim 14, wherein the actuating mechanism comprises manually operated rack and pinion gears.

16. A surgical device according to claim 15, wherein the extending mechanism comprises a rack formed on the proximal end of the non-rotating tine, a pinion gear engagable with the rack and a hand-operated driving gear engagable with the pinion.

17. A surgical device according to claim 14, wherein the extending mechanism is a manually operated push-pull device.

18. A surgical device according to claim 14, wherein the extending mechanism comprises: a rack formed on the proximal end of the non-rotating tine, a pinion gear engagable with the rack and a hand-operated driving gear engagable with the pinion.

* * * * *